(12) United States Patent
Jiang

(10) Patent No.: US 8,091,554 B2
(45) Date of Patent: Jan. 10, 2012

(54) METHODS AND DEVICES FOR RELIEVING UPPER AIRWAY OBSTRUCTIONS

(75) Inventor: Yandong Jiang, North Reading, MA (US)

(73) Assignee: The General Hospital Corporation, Boston, MA (US)

( * ) Notice: Subject to any disclaimer, the term of this patent is extended or adjusted under 35 U.S.C. 154(b) by 246 days.

(21) Appl. No.: 12/047,719

(22) Filed: Mar. 13, 2008

(65) Prior Publication Data

US 2008/0216843 A1 Sep. 11, 2008

Related U.S. Application Data

(63) Continuation-in-part of application No. 10/711,886, filed on Oct. 12, 2004, now abandoned, which is a continuation-in-part of application No. 10/769,180, filed on Jan. 30, 2004, now abandoned, application No. 12/047,719, which is a continuation-in-part of application No. 11/021,157, filed on Dec. 22, 2004, now abandoned, which is a continuation-in-part of application No. 10/769,180, filed on Jan. 30, 2004, now abandoned.

(51) Int. Cl.
| | |
|---|---|
| *A61M 15/00* | (2006.01) |
| *A61M 16/00* | (2006.01) |
| *A62B 7/00* | (2006.01) |
| *A62B 9/00* | (2006.01) |
| *A62B 18/00* | (2006.01) |
| *A62B 18/08* | (2006.01) |
| *A62B 18/02* | (2006.01) |
| *A62B 9/06* | (2006.01) |
| *A61F 5/37* | (2006.01) |
| *A61F 5/56* | (2006.01) |
| *A61F 11/00* | (2006.01) |
| *A61C 5/14* | (2006.01) |

(52) U.S. Cl. .............. 128/848; 128/200.24; 128/201.26; 128/204.26; 128/206.21; 128/206.24; 128/207.14; 128/846; 128/857; 128/861

(58) Field of Classification Search .................. 128/846, 128/857–863, 200.24, 200.26, 201.26, 204.26, 128/205.24, 206.21, 206.24, 207.14, 207.17; 602/902

See application file for complete search history.

(56) References Cited

U.S. PATENT DOCUMENTS 3,046,978 A 7/1962 Lea
(Continued)

FOREIGN PATENT DOCUMENTS

WO 97/31596 9/1997
(Continued)

OTHER PUBLICATIONS

P.J. Kahrilas et al., "Effect of Sleep, Spontaneous Gastroesophageal Reflux, and a Meal on Upper Esophageal Sphincter Pressure in Normal Human Volunteers," Gastroenterology, vol. 93, p. 466-471 (Jan. 1987).
(Continued)

*Primary Examiner* — Patricia Bianco
*Assistant Examiner* — Brandon Jackson
(74) *Attorney, Agent, or Firm* — Nutter McClennen & Fish LLP

(57) ABSTRACT

Methods and devices are provided that are effective to remove an obstruction in a human airway related to snoring and/or OSA. In one embodiment, the device includes mouthpiece having a hollow body configured to be disposed in a user's mouth. The body includes superior and inferior outer surfaces as well as anterior and posterior surfaces, a channel configured to receive a user's teeth formed in at least one of the superior and inferior surfaces, an inner cavity formed between the superior, inferior, anterior, and posterior surfaces, and at least one aperture formed in the posterior surface that extends into the inner cavity. In one exemplary embodiment the at least one aperture is oriented to extend away from the user's teeth and toward a user's tongue when the mouthpiece is in use. In another embodiment, the hollow body is substantially c-shaped, and the at least one aperture includes a plurality of apertures spaced a distance apart from one another along the posterior surface between first and second terminal ends of the c-shaped inner portion of the hollow body. In still another embodiment, the mouthpiece includes an outer portion having an opening extending therethrough such that the outer portion is coupled to the hollow body and is in fluid communication with the cavity in the hollow body. A one-way valve can be disposed in the opening and can be configured to allow air to flow out of a user's oral cavity when the mouthpiece is in use.

19 Claims, 12 Drawing Sheets

U.S. PATENT DOCUMENTS

| | | | |
|---|---|---|---|
| 3,742,939 A | 7/1973 | Sayer | |
| 4,270,531 A | 6/1981 | Blachly et al. | |
| 4,304,227 A | 12/1981 | Samelson | |
| 4,495,945 A * | 1/1985 | Liegner | 128/200.26 |
| 4,676,240 A | 6/1987 | Gardy | |
| 4,715,368 A * | 12/1987 | George | 128/859 |
| 4,821,712 A | 4/1989 | Gossett | |
| 4,995,388 A | 2/1991 | Brain et al. | |
| 5,117,816 A * | 6/1992 | Shapiro et al. | 128/200.24 |
| 5,243,971 A | 9/1993 | Sullivan et al. | |
| 5,269,296 A | 12/1993 | Landis | |
| 5,373,859 A | 12/1994 | Forney | |
| 5,560,354 A | 10/1996 | Berthon-Jones et al. | |
| 5,596,983 A | 1/1997 | Zander et al. | |
| 5,647,355 A | 7/1997 | Starr et al. | |
| 5,653,229 A | 8/1997 | Greenberg | |
| 5,720,302 A | 2/1998 | Belfer | |
| 5,752,510 A | 5/1998 | Goldstein | |
| 5,884,625 A | 3/1999 | Hart | |
| 5,954,048 A | 9/1999 | Thornton | |
| 5,957,133 A | 9/1999 | Hart | |
| 6,012,920 A | 1/2000 | Woo | |
| 6,070,581 A | 6/2000 | Augustine et al. | |
| 6,079,409 A | 6/2000 | Brain et al. | |
| 6,123,071 A | 9/2000 | Berthon-Jones et al. | |
| 6,183,423 B1 | 2/2001 | Gaumond et al. | |
| 6,209,542 B1 | 4/2001 | Thornton | |
| 6,212,435 B1 | 4/2001 | Lattner et al. | |
| 6,371,112 B1 | 4/2002 | Bibi | |
| 6,379,311 B1 | 4/2002 | Gaumond et al. | |
| 6,405,729 B1 | 6/2002 | Thornton | |
| 6,408,851 B1 | 6/2002 | Karell | |
| 6,494,209 B2 | 12/2002 | Kulick | |
| 6,536,424 B2 | 3/2003 | Fitton | |
| 6,571,798 B1 * | 6/2003 | Thornton | 128/206.21 |
| 6,618,627 B2 | 9/2003 | Lattner et al. | |
| 6,655,385 B1 | 12/2003 | Curti et al. | |
| 6,668,821 B2 | 12/2003 | Christopher | |
| 6,758,212 B2 | 7/2004 | Swann | |
| 6,789,543 B2 | 9/2004 | Cannon | |
| 6,887,513 B2 * | 5/2005 | Moritomo et al. | 427/130 |
| 6,918,388 B2 | 7/2005 | Brain et al. | |
| 7,021,312 B2 | 4/2006 | Cannon | |
| 7,328,705 B2 | 2/2008 | Abramson | |
| 8,020,276 B2 * | 9/2011 | Thornton | 29/464 |
| 2003/0121520 A1 * | 7/2003 | Parker et al. | 128/206.21 |
| 2003/0167018 A1 | 9/2003 | Wyckoff | |
| 2003/0168063 A1 | 9/2003 | Gambone et al. | |
| 2004/0045552 A1 | 3/2004 | Curti et al. | |
| 2004/0237965 A1 | 12/2004 | Bibi et al. | |
| 2005/0051176 A1 | 3/2005 | Riggins | |
| 2005/0103347 A1 | 5/2005 | Curti et al. | |
| 2005/0150504 A1 | 7/2005 | Heeke et al. | |
| 2005/0166928 A1 | 8/2005 | Jiang | |
| 2005/0166929 A1 | 8/2005 | Jiang | |

FOREIGN PATENT DOCUMENTS

| | | |
|---|---|---|
| WO | 03075739 | 9/2003 |

OTHER PUBLICATIONS

H. Gastaut, "Polygraphic Study of the Episodic Diurnal and Nocturnal (hypnic and respiratory) Manifestations of the Pickwick Syndrome," Brain Research, 2, p. 167-186 (1966).

J.E. Remmers et al., "Pathogenesis of Upper Airway Occlusion During Sleep," J. Appl. Physiology, 44(6) p. 290-293 (1978).

A.H. Goroll et al., "Primary Care Medicine: Office Evaluation and Management of the Adult Patient," 4th ed., p. 290-293, (2000).

W. Orr et al., "Effect of Sleep on Swallowing, Esophageal Peristalsis, and Acid Clearance," Gastroenterology, vol. 86, p. 814-819 (1986).

R. Walsh et al., "Upper Airway Obstruction in Obese Patients with Sleep Disturbance and Somnolence," Annals of Internal Medicine, vol. 76, p. 185-192, (1972).

D. Hudgel, "Variable Site of Airway Narrowing Among Obstructive Sleep Apnea Patients," J. Appl. Physiology, vol. 61(4), p. 1403-1409 (1986).

D.L. Morrison, "Pharyngeal Narrowing and Closing Pressures in Patients with Obstructive Sleep Apnea," Am Rev Respir Dis, vol. 148, pp. 606-611 (1993).

G. Don, "Site and Mechanics of Spontaneous, Sleep-Associated Obstructive Apnea in Infants," Journal of Applied Physiology, vol. 89, Issue 6, pp. 2453-2462 (2000).

International Search Report issued for PCT/US05/01530, publication No. WO2005/074484 A3, mailing date Jan. 4, 2006.

International Search Report issued for PCT/US05/01339, publication No. WO 2005/074480 A3, mailing date Aug. 18, 2005.

European Search Report issued for EP 05705768.9, dated Feb. 15, 2008.

Patent Office of the People's Republic of China, Office Action issued for CN 200580009566.X, issued Nov. 16, 2007.

* cited by examiner

METHODS AND DEVICES FOR RELIEVING UPPER AIRWAY OBSTRUCTIONS

CROSS-REFERENCE TO RELATED APPLICATIONS

The present application is a continuation-in-part of U.S. patent application Ser. No. 10/711,886 filed on Oct. 12, 2004 and entitled "Methods and Devices for Maintaining an Open Airway," which is a continuation-in-part of U.S. patent application Ser. No. 10/769,180 filed on Jan. 30, 2004 and entitled "Methods and Devices for Relieving Upper Airway Obstructions."

The present application is also a continuation-in-part of U.S. patent application Ser. No. 11/021,157 filed on Dec. 22, 2004 and entitled "Methods and Devices for Relieving Upper Airway Obstructions," which is a continuation-in-part of U.S. patent application Ser. No. 10/769,180 filed on Jan. 30, 2004 and entitled "Methods and Devices for Relieving Upper Airway Obstructions."

These references are hereby incorporated by reference in their entireties.

FIELD OF THE INVENTION

The present invention relates to methods and devices for reducing snoring and/or airway obstructive events, and in particular to methods and devices that are effective to generate a negative pressure in a patient's mouth to remove an upper airway obstruction and reduce or eliminate snoring and/or airway obstruction.

BACKGROUND OF THE INVENTION

Over 60 million Americans are affected by snoring and/or obstructive sleep apnea (OSA). During normal waking hours, muscle tone in most individuals unconsciously maintains the tongue, pharyngeal folds, soft palate, uvula, epiglottis and posterior pharyngeal wall in adequate spatial relationships so as not to interfere with the free passage of air. However, when asleep in the supine position, gravity can cause the tongue, soft palate, uvula, and epiglottis to move back toward the posterior pharyngeal wall. As a result, the size of the upper airway can be reduced and snoring may occur. Moreover, snoring may also be a sign that a person is suffering from OSA.

OSA is a condition where a person temporarily stops breathing for a short amount of time (10 seconds or longer) due to the blockage of the airway. During a customary sleep period a person suffering from OSA can experience hundreds of so called apneatic events, that is, periods when the person's airway becomes blocked until the patient's hypoxia becomes severe enough that the person awakens and resumes breathing normally again. Not only do these apneatic events cause a deficiency of restful sleep but, due to depleted oxygen levels, possible long term health problems, such as pulmonary hypertension, heart failure and stroke, can result.

One common non-invasive treatment approach for OSA is the use of a continuous positive airway pressure (CPAP) machine. A CPAP machine uses a nasal mask, harness or other headgear to continuously deliver pressured air directly to the person's windpipe, and the positive pressure prevents the upper airway from collapsing during sleep. While proven effective, most CPAP users often suffer from at least one of the following side effects: claustrophobia, difficulty exhaling, inability to sleep, nasal congestion, sore eyes, sore or dry throat, headaches, abdominal bleeding, chest muscle discomfort, nosebleeds and mask-related problems such as rash, skin abrasions and conjunctivitis from air leakage. Additionally, and especially during the early stages of usage, some people may have difficulty adjusting to both the mechanism and/or sound of the machine.

Alternatives to the CPAP machine include devices which can lock the tongue in a fixed position, such as metallic or hard plastic clips. However, these devices risk pain and injury to the tongue as well as are unsuited for self administration. Another alternative to the CPAP machine are mouthpieces that are effective to create an enlarged airway and/or hold the tongue in a fixed position using some type of retainer. While mouthpieces have had some success, normal swallowing can be interrupted, causing a reduction in the clearance of airway secretion, saliva aspiration, and even gastric reflex. Further, a mouthpiece may also cause temporomandibular joint pain to occur and can be detrimental to the normal bite relationship of the dental arches, since it distorts the relationship of the upper and lower jaws. More recently, some mouthpieces have attempted to use a vacuum to hold the tongue, or a portion thereof, in the retainer. However, these devices are often cumbersome and distracting to the sleeping patient. Further, should the patient swallow, the vacuum is broken and the tongue is pulled out of the retainer, resulting in an airway obstruction and a high degree of patient discomfort.

OSA can also cause problems for patients being treated for pulmonary and/or cardiac arrest, or patients undergoing general anesthesia. Typically, these patients are ventilated with a facemask that covers the nose and optionally the mouth. When the patient is under anesthesia or otherwise unconscious, however, the facemask can supply air, oxygen, or other gases to the patient only if the airway remains open. OSA can cause a closure of the airway due to the tongue falling back against the pharyngeal wall, thus preventing proper ventilation of the patient. Even for patients who do not have OSA, upper airway obstructions may develop once the patient is sedated. One solution for maintaining an open airway in patients is to use an endotracheal tube. This approach requires a rigid laryngoscope blade to be inserted into the patient's mouth. The endotracheal tube is then placed down into the trachea thereby holding the tongue away from the posterior pharyngeal wall. While this solution can be effective, successful intubation depends on deep sedation, muscle relaxation, strong analgesia and painful laryngoscopy. Intubation also is very uncomfortable, potentially causing the patient to suffer from a sore throat, as well as causing potential causing damage to the teeth, lips, tongue, vocal cords, and trachea. To terminate the general anesthesia, the patient has to be extubated, which also causes problems. During the critical period of extubation, the patient may develop tachycardia, hypertension, laryngospasm, hypoxia, nausea, vomiting, and even aspiration. Additionally, the patient may need to stay in the recovery room for a long period of time due to intubation and extubation.

More recently, one other solution has been the use of a laryngeal mask airway (LMA), which is inserted blindly into the pharynx and forms a low pressure seal around the laryngeal inlet. The complications from using LMA are similar to those using endotracheal tube. The sore throat resulted from using LMA may even worse than that from endotracheal tube intubation. While tracheal tubes and LMAs can be effective in maintaining an open airway in patients undergoing anesthesia or patients who otherwise having difficulty maintaining an open airway, these devices tend to be obtrusive, time-consuming, and uncomfortable. There are also potential complications that can result due to the use of these devices.

Accordingly, there remains a need for improved, non-invasive treatment methods and devices that are effective to remove upper airway obstructions, reduce or eliminate snoring and/or apneatic events and the related complications, and improve the patent's sleeping quality. There also remains a need for improved, non-invasive treatment methods and devices that are effective to maintain an open upper airway during anesthesia or other medical procedures and conditions in which it is necessary to maintain an open airway.

SUMMARY OF THE INVENTION

The present invention generally provides methods and devices that are effective to remove an obstruction in a human airway related to snoring and/or OSA. In one embodiment, the device includes a mouthpiece that is adapted to form a sealed cavity within a human mouth without impinging on a tongue in the mouth, and a hollow elongate member having a first end that is coupled to the mouthpiece and that is in communication with the sealed cavity, and a second end that is adapted to be coupled to a negative pressure generator. In use, a negative pressure generator can be attached to the hollow elongate member to remove air from the sealed cavity. When an obstructed airway occurs as a result of the collapse of the soft tissues of the upper airway, a negative pressure is created within the sealed cavity to pull the tongue and other soft tissues of the upper airway away from the posterior pharyngeal wall, thereby removing the obstruction. The "soft tissues of the upper airway" include, but are not limited to, the tongue, pharyngeal folds, soft palate, uvula, epiglottis and posterior pharyngeal wall.

While the mouthpiece can have a variety of configurations, in one embodiment it includes upper and lower portions that are adapted to conform to the anatomy of a human's upper and lower dental structures. The upper and lower portions of the mouthpiece are preferably connected to one another by a sidewall that extends therebetween to form the sealed cavity within the mouth. In another embodiment, the mouthpiece can include a sidewall that is adapted to be positioned over the opening of a human mouth, and a positioning member that is coupled to the sidewall and that is adapted to fit within the mouth to maintain the mouthpiece at a fixed position. The positioning member can include, for example, opposed first and second fixation elements that are adapted to be positioned between the upper and lower dental structures.

The present invention also provides a negative pressure generator for use within a mouthpiece or similar device that forms a sealed cavity within the patient's mouth. While the negative pressure generator can have a variety of configurations, in one embodiment it can be adapted to be operated by a patient's own breathing. In particular, the negative pressure generator can be in the form of a deformable member that is adapted to deform in response to inhalation, and that is biased to an original, un-deformed state such that return to the original, un-deformed state is effective to generate a negative pressure within the sealed cavity when an airway obstruction occurs. The negative pressure generator can also include at least one one-way valve that is adapted to control air flow into and out of the deformable member. A mating element, such as a strap or belt, can be used to releasably mate the deformable member to the patient.

In another embodiment, the present invention provides a method for removing an obstruction in a human airway by forming a sealed cavity within a human mouth and coupling the sealed cavity to a negative pressure generator. When an obstructed airway is caused by the collapse of the soft tissues of the upper airway, the negative pressure generator creates a negative pressure within the sealed cavity of the mouth to pull the tongue and/or soft tissues of the upper airway away from the posterior pharyngeal wall, thereby re-opening the obstructed airway.

In other aspects of the invention, a system is provided for maintaining an open airway, particularly during anesthesia. In one embodiment, the system includes a mouthpiece that is configured to form a substantially sealed cavity within a patient's mouth such that, when the mouthpiece is coupled to a negative pressure generator, a negative pressure can be created within the substantially sealed cavity to prevent the patient's soft tissues from falling against the posterior pharyngeal wall. The system can also include a nasal mask for communicating with the patient's nasal passages. The nasal mask can be used to deliver gases for placing the patient under anesthesia, and/or it can be used in combination with mechanical ventilation, CPAP, or positive end expiratory pressure (PEEP).

The present invention also provides a method for maintaining an open airway that includes the steps of forming a substantially sealed cavity within a patient's mouth, creating a negative pressure within the substantially sealed cavity effective to prevent the patient's soft tissues from falling against the posterior pharyngeal wall, and delivering gases through the patient's nasal passageway. The gases are preferably delivered simultaneously while a negative pressure is continuously generated within the patient's mouth to maintain an open airway.

In another embodiment, a mouthpiece is provided and includes a hollow body configured to be disposed in a user's mouth. The body includes superior and inferior outer surfaces as well as anterior and posterior surfaces, a channel configured to receive a user's teeth formed in at least one of the superior and inferior outer surfaces, an inner cavity formed between the superior, inferior, anterior, and posterior surfaces, and at least one aperture formed in the posterior surface that extends into the inner cavity. The at least one aperture can be oriented to extend away from the user's teeth and toward a user's tongue when the mouthpiece is in use. The at least one aperture can optionally include a mesh both disposed thereacross and configured to prevent a user's tongue from being pulled into the aperture. In one exemplary embodiment the hollow body can be substantially c-shaped. Further, the at least one aperture can include a plurality of apertures spaced a distance apart from one another along the posterior surface between first and second terminal ends of the c-shaped inner portion of the hollow body. The anterior surface of the hollow body can be configured to seal a user's oral cavity. The channel configured to receive the user's teeth can include a plurality of teeth-receiving apertures. In another embodiment the hollow body can include a channel formed in each of the superior and inferior surfaces. The channels can include a plurality of teeth-receiving apertures formed therein for receiving a user's upper and lower teeth. In still another embodiment the hollow body can include a channel formed in each of the superior and inferior surfaces such that the inferior surface is positioned anterior to the channel in the superior surface.

In other aspects, the mouthpiece can include an outer portion having an opening extending therethrough such that the outer portion is coupled to the hollow body and is in fluid communication with the cavity in the hollow body. In one exemplary embodiment the opening includes a one-way valve disposed therein and configured to allow air to flow out of a user's oral cavity when the mouthpiece is in use. The outer portion can be configured to form a seal around a user's oral cavity. In another embodiment the outer portion can include a flange configured to extend around a user's lips to seal the oral cavity. The flange can be spaced a distance apart from the hollow body for receiving a user's lips therebetween. An elongate member having a terminal end configured to couple to a negative pressure generator can be coupled to the opening in the outer portion of the mouthpiece.

In another embodiment, a mouthpiece is provided having first and second ridges that define a superior channel therebetween for receiving a user's upper teeth and an interior channel therebetween for receiving a user's lower teeth, with the first and second ridges each including an inner surface configured to contact a user's teeth adjacent the superior and inferior channels and an outer surface configured to be oriented away from the user's teeth. The mouthpiece can also include a hollow cavity formed between the superior and inferior channels, at least one aperture formed in the outer surface of the second ridge and extending into the hollow cavity, and an opening formed in the outer surface of the first ridge and extending into the hollow cavity such that the opening is configured to couple to a negative pressure generator. The negative pressure generator can be configured to apply a negative pressure through the opening to the at least one aperture to generate a negative pressure in a user's oral cavity for relieving an obstruction in a user's airway. In one embodiment, the superior and inferior channels can each include a plurality of teeth-receiving cavities formed therein. In another embodiment, the at least one aperture can include a plurality of apertures spaced along the outer surface of the second ridge. The at least one aperture can also optionally include a mesh extending thereacross and configured to prevent soft tissue from being pulled into the at least one aperture. In still another embodiment the mouthpiece can include a flange coupled to and positioned a distance apart from the outer surface of the first ridge. The flange can be configured to extend around a user's lips to seal a user's oral cavity.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a non-invasive remedy for snoring and/or OSA that is effective to generate a negative pressure within the oral cavity of a human to relieve an obstructed airway. The methods and devices are particularly advantageous for use with patients who suffer from snoring and/or OSA, or for patient's undergoing sedation or general anesthesia or other medical procedures in which it is necessary to maintain an open airway and/or relieve an obstruction. In particular, when a human, referred to herein as a patient, is sleeping in the supine position (or is otherwise unconscious), the soft tissues of the upper airway may fall against the posterior wall of the pharynx, thus blocking the air passageway. In response, the device of the present invention is effective to generate a negative pressure in the patient's mouth that pulls the patient's soft tissues of the upper airway apart to reopen the airway. The device is particularly advantageous in that, when a patient's upper airway is open, the negative pressure generator will remove only a small amount of air from the oral cavity without the creation of a negative pressure in the oral cavity, thus allowing the patient to breathe normally and comfortably. A negative pressure is only created when the airway is obstructed. Accordingly, the device does not impinge on the tongue, allowing free movement of the tongue when the airway is unobstructed, thereby reducing the risk of choking, coughing or aspiration due to excess saliva. The device can also optionally be used in combination with a nasal mask or other device effective to deliver gases to a patient's airway via the nasal passages.

Figure 1A:
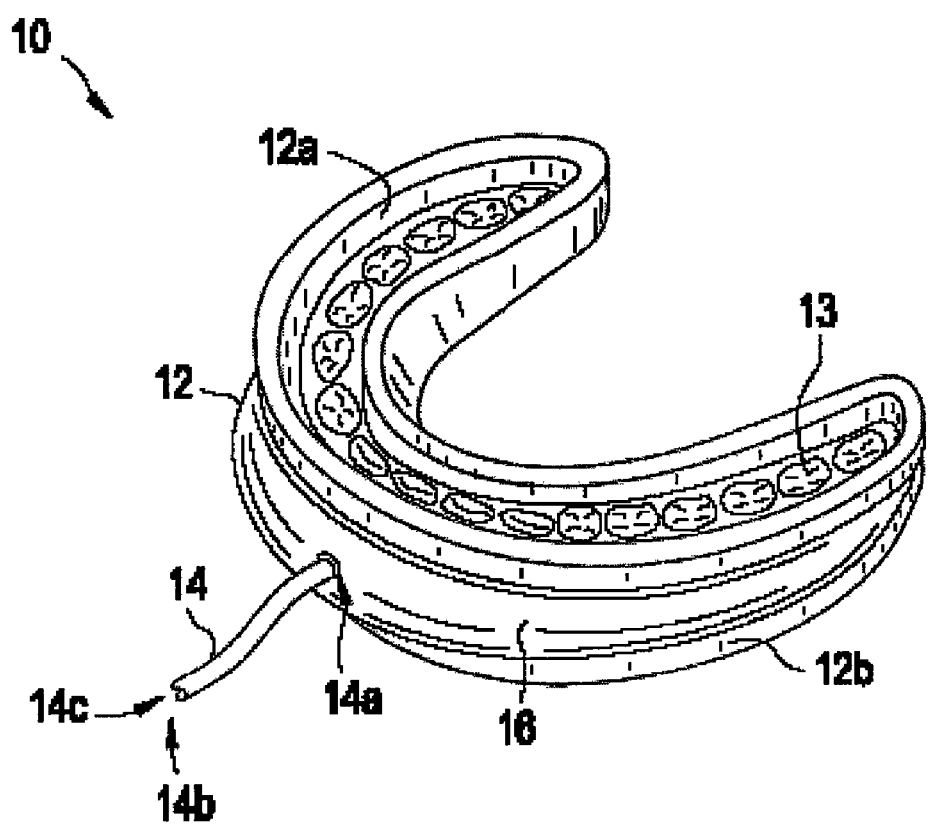
FIG. 1A is a side perspective view of one embodiment of a device for removing an airway obstruction in accordance with the present invention.
Figure 1B:
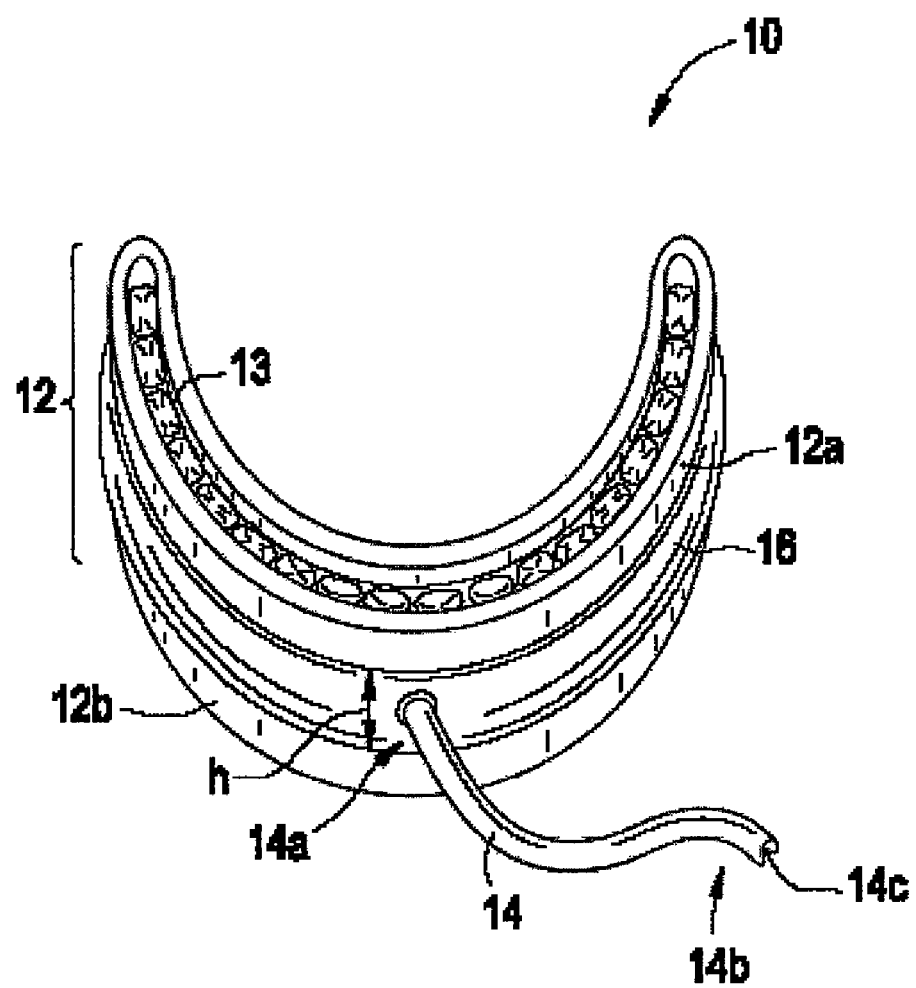
FIG. 1B is a front perspective view of the device shown in FIG. 1A.

FIGS. 1A and 1B illustrate an exemplary embodiment of a device 10 for removing an airway obstruction in accordance with the present invention. As shown, the device 10 generally includes a mouthpiece 12 that is adapted to fit within a patient's mouth and that is effective to form a sealed cavity within the patient's mouth, and a hollow elongate member 14 having a first end 14a that is coupled to the mouthpiece 12 and that is in communication with the sealed cavity, and a second end 14b that is adapted to couple to a negative pressure generator.

The mouthpiece 12 can have a variety of configurations, but it is preferably effective to create a sealed cavity within the patient's mouth to allow a negative pressure to be created therein in response to an obstructed airway. A sealed cavity can be formed by blocking the passage of air through the patient's mouth, such that the patient is prevented from breathing through the mouth. The sealed cavity should, however, be in communication with the patient's upper airway.

This will allow the negative pressure generator to create a negative pressure within the sealed cavity when an obstruction occurs in the patient's upper airway. A person skilled in the art will appreciate that it is possible to provide a mouthpiece in which some air is allowed to enter the patient's mouth. With such a configuration, however, the negative pressure generator should be operated at a pressure that is still sufficient to create a negative pressure within the cavity to separate the soft tissues from the posterior pharyngeal wall when an obstruction occurs.

In the illustrated embodiment, a sealed cavity is formed using a mouthpiece 12 that includes upper and lower portions 12a, 12b that are sized to fit around and/or to receive some or all of the upper and lower dental structures of the patient, including the gums and/or teeth, and a sidewall 16 that extends between the upper and lower portions 12a, 12b. Each portion 12a, 12b can have a variety of shapes and sizes and they can be individually molded to provide a custom fit, or, alternatively, each portion 12a, 12b can have a universal shape and size for use by most patients. The upper and lower portions 12a, 12b should, however, be effective to facilitate and maintain placement of the mouthpiece 12 in the patient's mouth. As shown in FIGS. 1A-1B, the upper and lower portions 12a, 12b are each substantially U-shaped, and they include cavities (only one cavity 13 is shown in upper portion 12a) formed therein for receiving the patient's teeth and/or gums. When positioned in the patient's mouth, the upper and lower portions 12a, 12b extend around the upper and lower incisors, canine teeth, and some of the pre-molar teeth.

The sidewall 16 that extends between the upper and lower portions 12a, 12b, can also have a variety of configurations, and it can be integrally formed with the upper and lower portions 12a, 12b, or it can be connected to the upper and lower portions 12a, 12b to mate the portions 12a, 12b to one another. The sidewall 16 should, however, extend between the upper and lower portions 12a, 12b such that it is positioned adjacent to the patient's lips when the mouthpiece 12 is in use. This will allow the sidewall 16 to prevent air from entering the patient's mouth, thus allowing a negative pressure to be created in the patient's mouth in response to a blocked airway.

Figure 2:
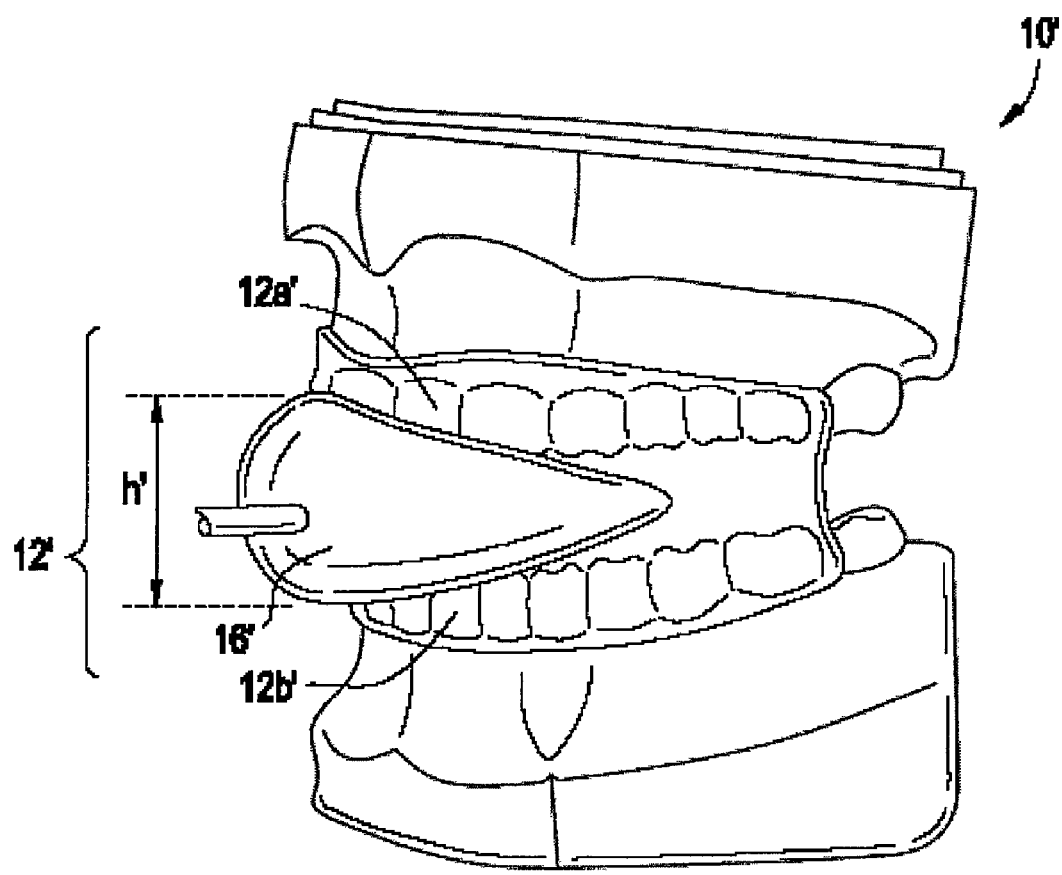
FIG. 2 is a side view of a device for removing an airway obstruction having an expanded sidewall in accordance with another embodiment of the present invention.

In another embodiment of the present invention, the sidewall 16 can be adapted to expand the size of the oral cavity or sealed cavity in the patient's mouth. An expanded oral cavity allows the tongue and/or soft palate to be pulled a greater distance away from the posterior pharyngeal wall, thus making it more difficult for the tongue and other soft tissues to form a complete blockage of the upper airway when they collapse. This is particularly advantageous for patients having a relatively small oral cavity, a large tongue, and/or patients lacking teeth. While a variety of techniques can be used to expand the size of the oral cavity, in one embodiment the sidewall 16 can be configured to maintain the patient's dental structures in a fixed relationship with respect to one another. In particular, the sidewall 16 can have a height h that extends between the upper and lower portions 12a, 12b of the mouthpiece 12 such that the patient's dental structures are positioned a distance apart from one another that is substantially equal to the height h of the sidewall 16, as shown in FIG. 1B. In another embodiment, as shown in FIG. 2, the sidewall 16, can be in the form of a protrusion that extends between the upper and lower portions 12a', 12b' and that protrudes through the mouth of the patient such that part of the sidewall 16' is positioned between the patient's lips. The protruding sidewall 16' can vary in shape and size, but in an exemplary embodiment it is substantially rounded and it has a width (not shown) that allows the sidewall 16' to extend between opposed edges of a patient's lips, and a height h' that is effective to maintain the patient's upper and lower dental structures at a fixed distance apart from one another. A person skilled in the art will appreciate that the mouthpiece can have a variety of other configurations to expand the size of a patient's oral cavity.

For example, in another embodiment (not shown), the sidewall 16 can extend at an angle from top portion 12a, 12a' to lower portion 12b, 12b' such that the lower portion 12b, 12b' holds the lower jaw in a forward position relative to its resting state, so as to expand the size of the oral cavity or sealed cavity in the patient's mouth. One skilled in the art will appreciate that the extent by which the lower portion may be advanced or displaced with respect to the upper portion will vary depending on the needs and anatomy of individual patients. In one aspect the lower portion may be advanced with respect to the upper portion by an amount in the range of about 0.25 mm to 30 mm, more preferably in the range from about 2 mm to 14 mm, and most preferably in the range from about 4 mm to 6 mm. A person skilled in the art will also appreciate that the mouthpiece can be configured to adjust any amount of advancement of the lower portion with respect to the upper portion by any suitable amount, for example within the range of about 0 to 30 mm. A variety of mechanisms can be used to allow relative movement between the upper and lower portions, and to lock the lower portion in a desired position relative to the upper portion. Such devices include, but are not limited to, screws, slides, pins, rubber bands, etc.

Referring back to FIGS. 1A and 1B, the device 10 also includes a hollow elongate member 14 that is coupled to the mouthpiece 12 and that is in communication with the sealed cavity. The hollow elongate member 14 can have a variety of shapes and sizes, but it should be effective to provide a passageway between the sealed cavity in the patient's mouth and a negative pressure generator. In an exemplary embodiment, the hollow elongate member 14 has a generally tubular shape and it includes a first end 14a that is mated to the mouthpiece 12, and a second end 14b that is adapted to couple to a negative pressure generator. The first end 14a can be removably or fixedly attached to any portion of the mouthpiece 12, but in an exemplary embodiment it is fixedly attached to the sidewall 16 of the mouthpiece 12, preferably at a substantial midpoint thereof, as shown in FIGS. 1A-1B. The hollow elongate member 14 is also preferably coupled to the mouthpiece 12 adjacent to an opening of the patient's mouth, such that the hollow elongate member 14 does not extend into the patient's mouth. The length and flexibility of the hollow elongate member 14 can also vary, but it should have a length and flexibility that does not restrict movement of the patient during use. The length should also be sufficient to allow a negative pressure generator, which is attached to the second end 14b of the hollow elongate member 14, to be positioned a distance apart from the patient.

The hollow elongate member 14 also includes an inner lumen 14c extending therethrough between the first and second ends 14a, 14b. The inner lumen 14c is in communication with the sealed cavity in the patient's mouth and the negative pressure generator, thus allowing the negative pressure generator to create a negative pressure within the sealed cavity. The inner lumen 14c can vary in shape and size, but the size should be adapted to allow a negative pressure generator to remove air from the patient's mouth at a rate that is effective to create a negative pressure in the sealed cavity only when an airway obstruction occurs, and to otherwise allow normal breathing and swallowing by the patient. A person skilled in the art will appreciate that the hollow elongate member 14 can have a variety of other configurations, and moreover that a variety of techniques can be used to couple the sealed cavity to a negative pressure generator.

Figure 3:
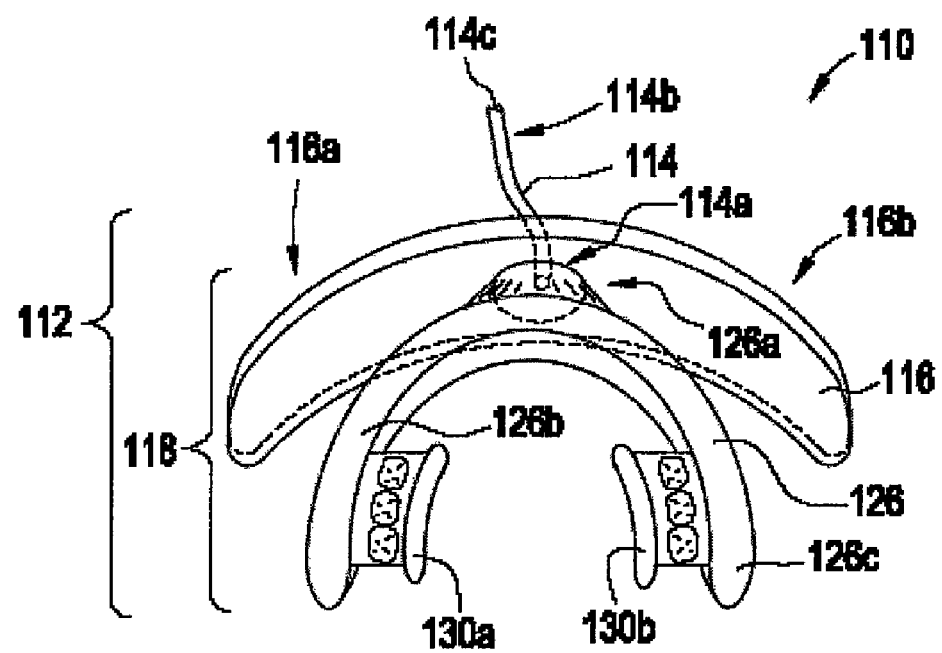
FIG. 3 is a top perspective view of yet another embodiment of a device for removing an airway obstruction having a positioning member in accordance with the present invention.

By way of non-limiting example, FIG. 3 illustrates yet another embodiment of a device 110 for removing an airway obstruction. In this embodiment, the device 110 includes a mouthpiece 112 having a sidewall 116 that is adapted to be positioned over the opening of the patient's mouth, rather than within the patient's mouth as described in connection with FIGS. 1A-2. The device 110 also includes a positioning member 118 that is adapted to fit within the patient's mouth to maintain the mouthpiece 112 at a fixed position. A hollow elongate member 114 is coupled to the mouthpiece 112 and it is adapted to provide communication between the sealed cavity and a negative pressure generator. In use, the device 110 operates similar to device 10 (described above in connection with FIGS. 1A-2) in that the sidewall 116 of the mouthpiece 112 prevents air from entering the patient's mouth, thus allowing a negative pressure to be created in the patient's mouth in response to a blocked airway.

While the sidewall 116 of the mouthpiece 112 can have a variety of shapes and size, FIG. 3 illustrates a substantially oval, elongate sidewall 116 that conforms to an external portion of a patient's face. More particularly, the sidewall 116 includes opposed ends 116a, 116b that are preferably angled toward one another and that fit around the area on opposed sides of a patient's lips. The sidewall 116 can also optionally include one or more cavities (not shown) formed therein for seating at least a portion of the patient's lips and/or surrounding facial structures.

As stated above, the mouthpiece 112 also includes a positioning member 118 that is connected to the sidewall 116, and that is effective to maintain the mouthpiece 112 at a fixed position with respect to the patient's mouth. While the positioning member 118 can have a variety of configurations, in the illustrated embodiment the positioning member 118 includes a connecting wall 126 that is coupled to a substantial mid-portion of the sidewall 116, and that is adapted to extend into the patient's mouth. The connecting wall 126 has a first, substantially cylindrical portion 126a that is mated to the sidewall 116, and a second portion having opposed extension members 126b, 126c. The first portion 126a is configured to fit between the patient's lips, and the extension members 126b, 126c are configured to extend into the patient's mouth such that they are positioned on opposed sides of the patient's upper and lower dental structures. Each extension portion 126b, 126c can optionally include a fixation element 130a, 130b formed thereon and adapted to be positioned between the upper and lower dental structures of the patient. In an exemplary embodiment, the fixation elements 130a, 130b are adapted to conform to the patient's canine and/or molar teeth to allow the patient to bite down on the fixation elements 130a, 130b, thus maintaining the position of the mouthpiece 112 within the patient's mouth.

A person skilled in the art will understand that the embodiment illustrated in FIG. 3 can be modified in various ways. For example, the fixation elements 130a, 130b need not be present and/or extension portion 126b, 126c do not need to extend as far back as the opposite sides of the patient's dentures as the device can seal the oral cavity simply by contacting and conforming to the lips and/or oral cavity.

The device 110 also includes a hollow elongate member 114 which provides a passageway between the sealed cavity in the patient's mouth and a negative pressure generator. The hollow elongate member 114, which is similar to hollow elongate member 14 described above in connection with FIGS. 1A-1B, has a first end 114a coupled to the mouthpiece 112 at a substantial mid-portion of the sidewall 116 such that the inner lumen 114c in the hollow elongate member 114 is in communication with the sealed cavity formed within the patient's mouth, and a second end 114b adapted to mate to a negative pressure generator.

Figure 4A:
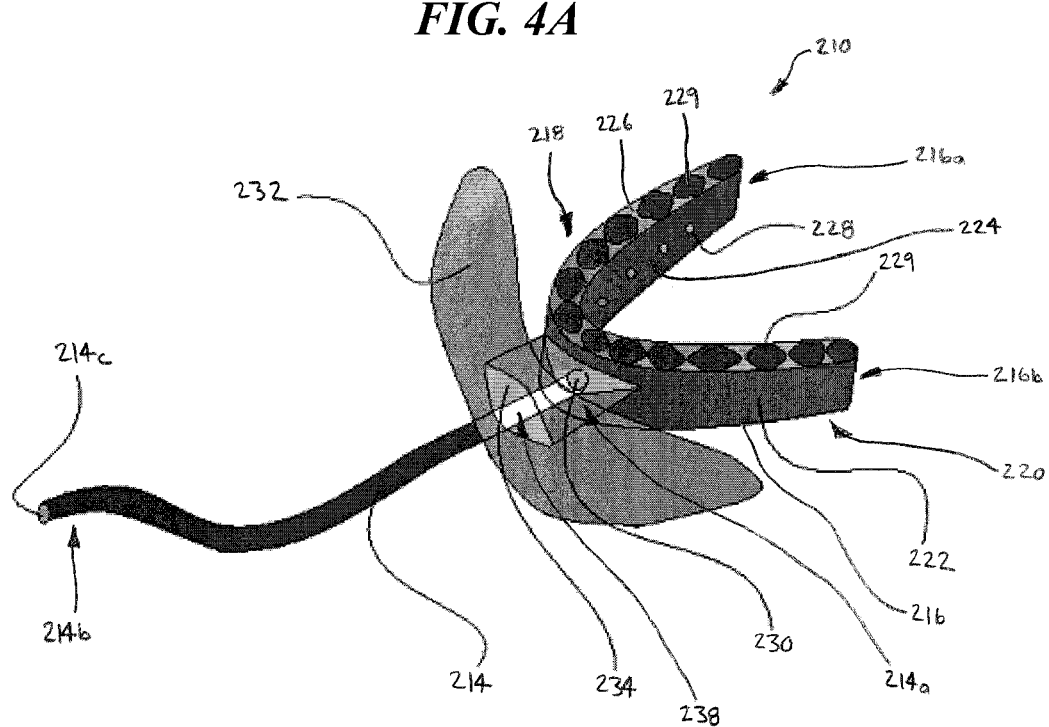
FIG. 4A is perspective view of yet another embodiment of a device for removing an obstruction in an airway having a plurality of apertures formed therein.
Figure 4B:
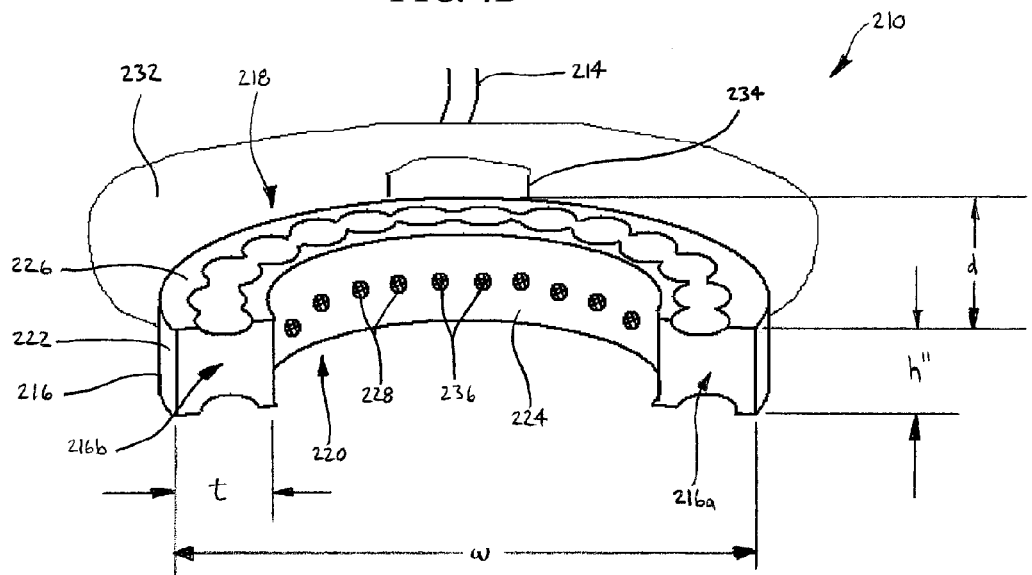
FIG. 4B is a perspective view of another embodiment of the device of FIG. 4A having mesh disposed across air apertures formed therein.
Figure 4C:
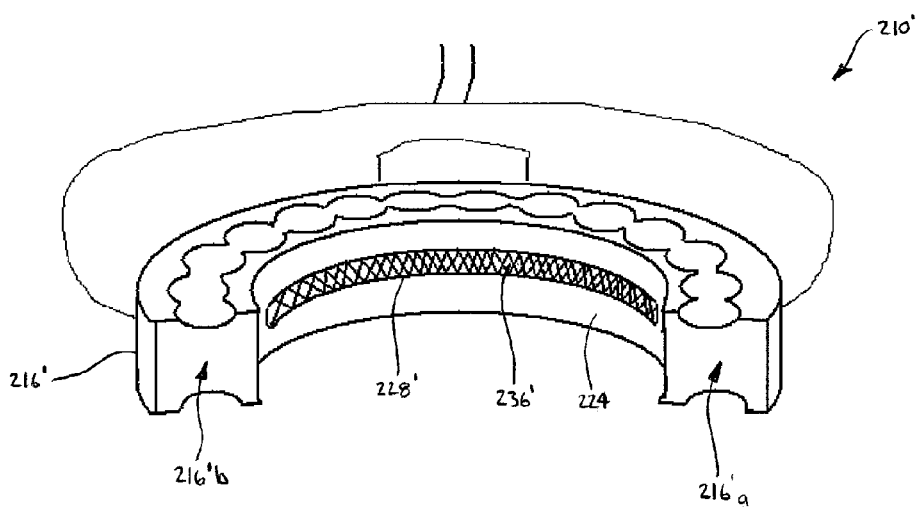
FIG. 4C is a perspective view of another embodiment of a device for removing an obstruction in an airway having a single elongate air aperture with mesh disposed thereacross.

FIGS. 4A-4C illustrate yet another exemplary embodiment of a device 210, 210' for removing an airway obstruction. In the embodiment illustrated in FIGS. 4A and 4B the device 210 generally includes a mouthpiece having a hollow body 216 configured to be disposed in a mouth. The hollow body 216 includes an inner cavity (not illustrated) formed between superior and inferior outer surfaces 218, 220 and anterior and posterior surfaces 222, 224 of the hollow body 216. A channel 226 configured to receive teeth and/or gums can be formed in at least one of the superior and inferior surfaces 218, 220. Further, at least one aperture 228 can be formed in the posterior surface 224 of the hollow body 216 and can extend into the inner cavity. An opening 230 can be located on the anterior surface 222 of the hollow body 216 that is in fluid communication with the inner cavity and thus the at least one aperture 228. The opening 230 can be adapted to receive a negative pressure. The device 210 can also include an outer portion 232 coupled to the hollow body 216. The outer portion 232 can include an opening 238 extending therethrough and configured to couple to the opening 230 on the anterior surface 222 of the hollow body 216. A connector, such as a one-way valve 234, can extend between the hollow body 216 and the outer portion 232 to couple the opening 230 in the hollow body 216 with the opening 238 in the outer portion 232 to allow air to flow therethrough. In use, the device 210 operates similar to devices 10, 10', 110 described above in connection with FIGS. 1A-3 in that the hollow body 216 and/or the outer portion 232 prevents air from entering the patient's mouth, thus allowing a negative pressure to be created in the patient's mouth in response to a blocked airway.

The hollow body 216 can have a variety of shapes and sizes but it is preferably adapted to be disposed in a user's mouth. As indicated above, the hollow body 216 can include superior and inferior outer surfaces 218, 220 and anterior and posterior surfaces 222, 224. A multitude of other surfaces can further define the hollow body 216 depending on the shape and intended use of the hollow body 216. The hollow body 216 can serve as a barrier to prevent the communication of air in and out of the oral cavity, and more particularly, the anterior surface 222 can effectively seal a user's oral cavity. The anterior and posterior surfaces 222, 224 can be in the form of laterally-extending first and second walls or ridges that are spaced a distance apart from one another to form the inner cavity therebetween. The first and second ridges can be substantially c-shaped between terminal ends 216a, 216b such that they are configured to be positioned on opposed sides of and extend around a user's teeth. Further, the first and second ridges can include inner surfaces that are configured to contact a user's teeth, and outer surfaces that are oriented away from the user's teeth. Alternatively, the inner surfaces can be configured to contact a user's gums when teeth are not present. The superior and inferior surfaces 218, 220 can extend between and connect the anterior and posterior surfaces 222, 224. The superior and inferior surfaces can be formed by two walls spaced longitudinally apart from one another such that the inner cavity is formed between all four surfaces. The position of the walls that form the superior and inferior surfaces 218, 220 relative to the ridges that form the anterior and posterior surfaces 222, 224 can define superior and/or inferior channels for receiving teeth, or the superior and inferior surfaces can include one or more cut-outs formed therein to form channels for receiving a user's teeth and/or a user's gums.

The channel configured to receive teeth and/or gums can have various configurations. In the illustrated embodiment each of the superior and inferior surfaces 218, 220 includes an elongate channel (only one channel 226 is shown) formed therein. The channels can be sized to fit around and/or to receive some or all of the upper and lower dental structures of a user, including the gums and/or teeth. The channels can have a variety of shapes and sizes and can be individually molded to provide a custom fit, or alternatively the channels can have a universal shape and size that is flexible for use by most users. The channels should, however, be effective to facilitate and maintain placement of the mouthpiece in the user's mouth. As illustrated, the channels can include individual cavities 229 formed therein for receiving the user's teeth and/or gums. Alternatively, the channels can have a single elongate open configuration for receiving a user's teeth. When positioned in the patient's mouth, in an exemplary embodiment the channels receive the upper and lower incisors, canine teeth, and some of the pre-molar teeth. In another exemplary embodiment, the hollow body 216 can be configured to force a user's lower jaw to protrude more forward than the user's upper jaw and hold it in such a position, thereby increasing the amount of space in the user's pharyngeal cavity. More particularly, the inferior surface 220 or the channel formed therein can be offset from the superior surface 218 or the channel 226 formed therein to achieve such a configuration. In one embodiment, portions of the inferior surface 220 or the channel formed therein can be made of a harder material than other portions of the device 210 to assist with holding a patient's lower jaw in a more forward location. The hollow body 216 can also be configured to expand the size of the oral cavity or sealed cavity in the user's mouth. For example, the hollow body 216 can include space between the walls that define the superior and inferior surfaces 218, 220, thereby expanding the size of the oral cavity. In other words, the anterior and posterior surfaces 222, 224 can have a height that is significantly greater than a distance between the patient's upper and lower teeth or gums. One skilled in the art will appreciate that the extent by which the lower jaw may be advanced or displaced with respect to the upper jaw will vary depending on the needs and anatomy of individual patients. In one aspect the lower jaw may be advanced with respect to the upper jaw by an amount in the range of approximately 0.25 mm to 30 mm, more preferably in the range from approximately 2 mm to 14 mm, and most preferably in the range from approximately 4 mm to 6 mm. A person skilled in the art will also appreciate that the device 210 can be configured to adjust any amount of advancement of the lower jaw with respect to the upper jaw by any suitable amount, for example within the range of approximately 0 to 30 mm.

While the size of the hollow body 216 can vary to maintain a desired distance between the upper and lower teeth, in an exemplary embodiment the hollow body 216 is configured to maintain the teeth a distance apart in the range of approximately 1 mm to 15 mm. Likewise, other dimensions of the hollow body 216 can also vary depending on factors such as the size of the user's mouth, the intended use of the device 210 for a particular user, and the shape of the hollow body 216. For example, a user that is a baby will typically use a device 210 that is smaller than a user that is an adult. In other instances, it may be desirable to only have the device 210 extend over a portion of the teeth, for example only between the incisors or the canines. Generally, with respect to a substantially c-shaped hollow body 216, the depth d of the hollow body 216, defined as the distance from a front most portion of the anterior surface 222 of the hollow body 216 to the terminal ends 216a, 216b, can be in the range of approximately 10 mm to 200 mm, the length of the hollow body 216 from one terminal end 216a to the other terminal end 216b if the hollow body 216 were straightened can be in the range of approximately 20 mm to 300 mm, the width w of the hollow body 216 from the outside of one terminal end 216a to the other terminal end 216b can be in the range of approximately 10 mm to 200 mm, the height h″ of the hollow body 216 from the superior surface 218 to the inferior surface 220 can be in the range of approximately 2 mm to 20 mm, and the thickness t of the hollow body 216 from the anterior surface 222 to the posterior surface 224 can be in the range of approximately 3 mm to 15 mm. The dimension of any particular aspect of the device 210 does not have to be uniform throughout the device 210. By way of non-limiting example, the height h″ of the hollow body can be different at a location near the opening 230 and a location near one of the terminal ends 216a, 216b, or alternatively, the height h″ of the hollow body can be different at each of the terminal ends 216a, 216b.

As indicated above, an opening 230 can be formed in the anterior surface 222 of the hollow body 216. The opening 230 can allow for a negative pressure to be applied to inner cavity in the hollow body 216 and thus to the patient's oral cavity by way of one or more apertures 228 formed in the posterior surface 224 of the hollow body 216. While the opening 230 can have a variety of shapes and sizes, it preferably has a diameter in the range of approximately 10 to 20 mm.

As illustrated in FIGS. 4A and 4B, the posterior surface 224 can include multiple apertures 228 spaced a distance apart from one another along the posterior surface 224 between the first and second terminal ends 216a, 216b. The apertures 228 can be located anywhere along the posterior surface 224, including at any height of the posterior surface 224 between the superior and inferior surface 218, 220 so long as the apertures 228 are positioned to extend into the inner cavity for receiving a negative pressure. In an alternative embodiment, illustrated in FIG. 4C, a single elongated aperture 228' can extend between the first and second terminal ends 216'a, 216'b of the hollow body 216'. Regardless of the number of apertures, or the size and shape of those apertures, in an exemplary embodiment the apertures 228, 228' extend away from a user's teeth and toward a user's tongue when the device 210, 210' is in use. Further, one or more of the apertures 228, 228' can be configured to prevent a user's tongue from being pulled into the aperture 228, 228' when a negative pressure is being applied thereto. One way this can be accomplished is by placing a material, such as a mesh 236, 236', across one or more of the apertures 228, 228'.

While the dimensions of the apertures 228, 228' will depend on a number of different factors, such as for example the number of apertures, the size of the hollow body 216, 216', and the amount of negative pressure being applied through the hollow body 216, 216', in the embodiment illustrated in FIGS. 4A and 4B, each aperture 228 preferably has a diameter in the range of approximately 1 mm to 5 mm and is spaced apart by approximately 3 mm, and preferably no more than 10 mm. A person skilled in the art will appreciate that the apertures 228 do not need to be the same size or shape and do not need to be equally spaced apart. In the embodiment illustrated in FIG. 4C, the single elongate aperture 228' has a height in the range of approximately 1 mm to 5 mm and a length in the range of approximately 10 mm to 300 mm. Again, a person skilled in the art will appreciate that the single aperture 228' does not need to extend across the entire posterior surface 224', but instead can extend across one or more discrete portions (i.e., in the form of one or more elongate apertures), and further, can have a variety of different shapes and sizes depending on a particular patient and/or a particular use.

Figure 4D:
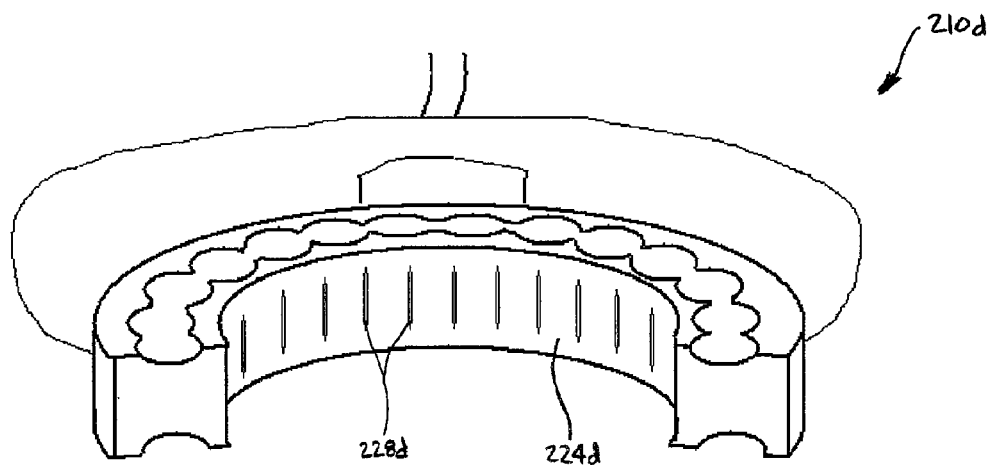
FIG. 4D is a perspective view of another embodiment of a device for removing an obstruction in an airway having a plurality of slots formed therein.
Figure 4E:
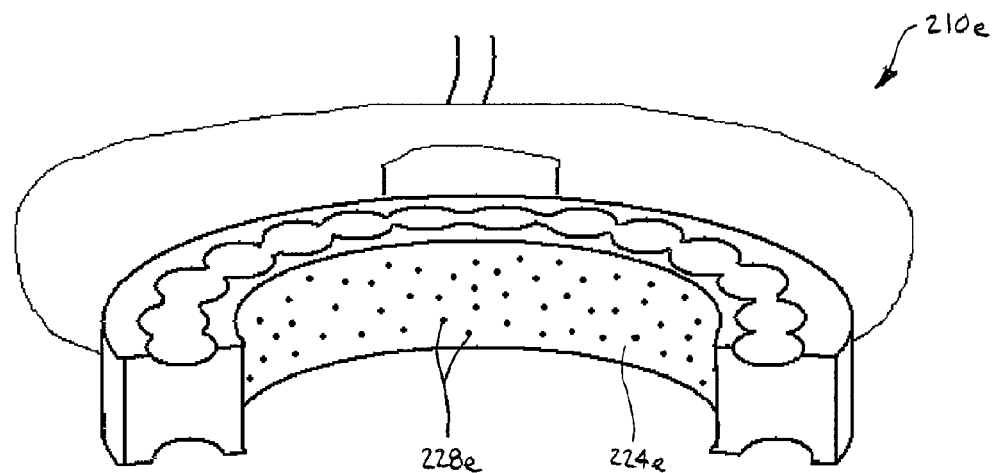
FIG. 4E is a perspective view of another embodiment of a device for removing an obstruction in an airway having a plurality of perforations formed therein.
Figure 4F:
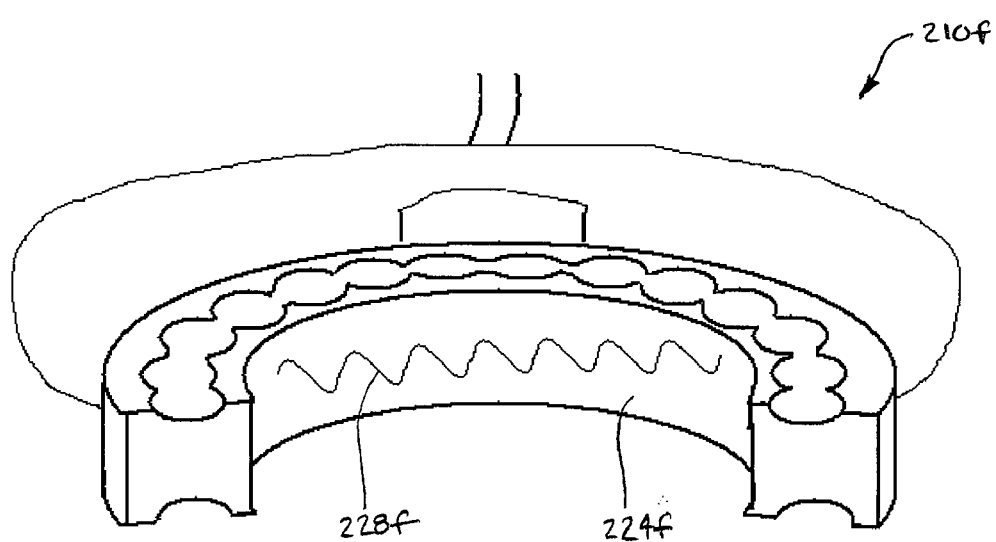
FIG. 4F is a perspective view of another embodiment of a device for removing an obstruction in an airway having a line shaped approximately like a sine wave formed therein.

FIGS. 4D-4F illustrate other embodiments of devices 210d, 210e, 210f that are similar to the devices 210, 210' but include other designs in place of the apertures 228, 228'. For example, in FIG. 4D, the posterior surface 224d of the device 210d can include multiple vertical slots 228d spaced a distance apart from one another along the posterior surface 224d for allowing a negative pressure to be applied to a user's oral cavity. The vertical slots can have a height in the range of approximately 1 mm to 15 mm, can have a thickness in the range of approximately 0.1 mm to 5 mm, and can be spaced apart by a range of approximately 2 to 10 mm. Alternatively, as illustrated in FIG. 4E, the posterior surface 224e of the device 210e can include multiple perforations 228e disposed therein for allowing a negative pressure to be applied to a user's oral cavity. The perforations can have a diameter in the range of approximately 0.1 mm to 5 mm and can be disposed on the posterior surface 224e in any desirable configuration, or in no particular configuration at all. In another alterative embodiment illustrated in FIG. 4F, the posterior surface 224f of the device 210f can include one or more longitudinal lines 228f formed therein. In the illustrated embodiment the line 228f is approximately in the shape of a sine wave, but any line(s) or shape(s), or combination thereof, could be used to allow a negative pressure to be applied to a user's oral cavity. The thickness of the one or more lines can be in the range of approximately 0.1 mm to 5 mm. While a mesh or similar material can be disposed across any of the slots 228d, perforations 228e, and lines 228f, when the thickness is small, as illustrated in FIGS. 4D-4F, such a mesh or similar material is not generally a useful addition to the devices 210d, 210e, and 210f. A person skilled in the art would recognize that these different designs are not all inclusive and that many other designs could also be incorporated to allow a negative pressure to be applied to a user's oral cavity. Further, one or more of the disclosed apertures 228, 228', slots 228d, perforations 228e, lines 228f, or other shapes and designs can be used together in the posterior surface of a single device.

In some embodiments an outer portion 232 can be coupled to the hollow body 216 and can be in fluid communication with the cavity of the hollow body 216 by way of an opening 238, as will be discussed in more detail below. While the outer portion 232 can have a variety of shapes and sizes, in the illustrated embodiment the outer portion is in the form of an elongate wall or flange. The outer portion 232 can form a seal around a patient's oral cavity and/or it can be adapted to conform to an external portion of the user's face. The flange can be located a distance apart from the hollow body to receive a user's lips therebetween. Alternatively, the flange can be located substantially flush to the anterior surface 222 of the hollow body 216 and can include a recess or cavity formed therein for receiving the user's lips. While not shown, a head strap can optionally be attached to the flange to secure the device 210 in place. As indicated above, the outer portion 232 can include an opening 238. The opening 238 can be formed in any portion of the outer portion 232 but preferably extends through the outer portion 232 to provide communication from one side of the outer portion 232 to the other side. The opening 238 can have any shape or size that allows fluid to flow through the outer portion 232. For example, the opening 238 can be in the form of a slot or an ellipse, or as illustrated, can have a generally circular shape that extends through the outer portion 232. In an exemplary embodiment the diameter of the opening 238 of the outer portion 232 is in the range of approximately 10 mm to 20 mm.

As shown in FIG. 4A, a connector can be disposed between the outer portion 232 and the hollow body 216 and it can be configured to couple the respective openings 238, 230. In an exemplary embodiment, the connector can include or be in the form of a valve 234 that is effective to control the flow of fluid into and out of the cavity in the hollow body 216. As illustrated, one end of the valve 234 is coupled to the anterior surface 222 of the hollow body 216 and is in fluid communication with the opening 230 in the anterior surface 222, and the other end of the valve 234 is coupled to the outer portion 232 and is in fluid communication with the opening 238 in the outer portion 232. The valve 234 can be a one-way valve that is configured to allow air to flow out of a user's oral cavity when the device 210 is in use and prevent flow into the cavity of the hollow body 216. More particularly, the valve 234 can have a low resistance and high flow capacity. In one embodiment the maximal flow is 160 liters per minute. Generally, the valve 234 can be configured such that, when pressure in the oral cavity is higher than ambient pressure, the valve 234 opens and allows air to flow out of the oral cavity, and when pressure in the oral cavity is equal to or lower than the ambient pressure, the valve 234 remains closed and air cannot flow out of the oral cavity. When the valve 234 is closed and there is no out-flow of air by the user the air can be suctioned out through the valve 234 and into the associated negative pressure generator. Accordingly, the user can exhale, and even cough, without disturbing the location of the device 210 so that such actions do not cause the device 210 to disengage from the mouth.

Similar to the devices 10, 10', and 110, the device 210 can also be configured to couple to or can include a hollow elongate member 214 that provides a passageway between the sealed cavity in the user's mouth and a negative pressure generator. The hollow elongate member 214, which is similar to hollow elongate member 14, 114 described in connection with FIGS. 1A-1B and 3, has a first end 214a coupled to the opening 238 of the outer portion 232 and/or directly to the valve 234 such that an inner lumen 214c in the hollow elongate member 214 is in fluid communication with the sealed cavity formed within the user's mouth via the apertures 228 in the anterior surface 222 of the hollow body 216. The hollow elongate member 214 also has a second end 214b adapted to mate to a negative pressure generator. As with the other devices 10, 10', and 110, the negative pressure generator can generate a negative pressure in the oral cavity to assist in preventing the tongue from falling back to the posterior pharyngeal wall, thereby clearing a passageway for the user to breath. In embodiments that do not include the outer portion 232, the hollow elongate member 214 can be configured to couple directly to the opening 230 of the hollow body 216, or to a valve disposed therein or mated thereto.

As previously stated, the devices in accordance with the present invention are preferably used in connection with a negative pressure generator that is effective to create and maintain a negative pressure in the sealed cavity in the user's mouth. While virtually any negative pressure generator that is effective to withdraw air and/or fluid from a sealed cavity can be used, by way of non-limiting example the negative pressure generator can be a vacuum pump. Alternatively, the negative pressure generator can be a device that is operated using energy generated from the user's own breathing, and FIG. 5 illustrates an exemplary embodiment of one such device.

Figure 5:
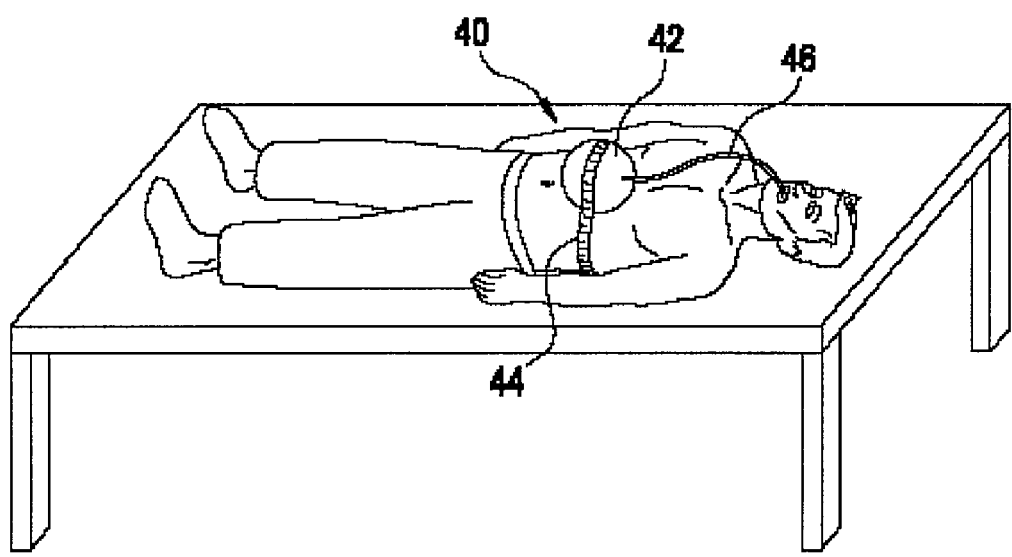
FIG. 5 is a side perspective view of one embodiment of a negative pressure generator that is coupled to a human chest, and that is operated by the human breathing.

As shown in FIG. 5, the negative pressure generator 40 is in the form of a deformable member 42 that is positioned on the patient's chest, and that is preferably held there by a mating element 44. In use, the deformable member 42 is effective to deform when the patient's chest expands due to inhalation, and it is biased to an original, non-deformed state. This will allow the deformable member 42 to draw in air from the sealed cavity in the patient's mouth as the deformable member 42 transitions from a deformed state to its original, non-deformed state, thus creating a negative pressure within the sealed cavity. While the deformable member 42 can have virtually any shape and size, in the illustrated embodiment the deformable member 42 has a generally spherical shape, such that a hollow cavity formed within the deformable member 42 is in communication with a sealed cavity in the patient's mouth.

The deformable member 42 also preferably includes a first one-way valve (not shown) that is adapted to control air flow from the sealed cavity in the patient's mouth, to the inner cavity in the deformable member 42. In particular, the first one-way valve, allows air to be drawn in from the sealed cavity, yet it does not allow air to flow in a reverse direction from the deformable member to the sealed cavity. A second one-way valve is also preferably provided to allow air to be released into the environment as the deformable member 42 deforms, yet to prevent air from being drawn in from the surrounding environment as the deformable member 42 returns to the original, non-deformed state. Accordingly, the first and second one-way valves work in conjunction with one another to control air flow to allow a negative pressure to be created in the sealed cavity in the patient's mouth. In an exemplary embodiment, the first one-way valve is disposed between a hollow elongate member 46 that extends from the sealed cavity to the deformable member 42, and the second one-way valve is disposed at a location on the deformable member 42 that allows air to be released into the surrounding environment.

As previously stated, the deformable member 42 also preferably includes a mating element 44 that is effective to at least temporarily retain the deformable member 42 on the patient's chest during use of the device. While a variety of techniques can be used to couple the deformable member 42 to the patient's chest, FIG. 5 illustrates a strap or belt 44 that is disposed around both the patient's midsection and the deformable member 42, and that is effective to releasably secure the deformable member 42 to the patient's chest. A person skilled in the art will appreciate that virtually any technique can be used to couple the deformable member 42 to the patient's chest including, for example, a jacket that contains the deformable member 42 and that is wearable by the patient.

In use, the deformable member 42 is coupled to the sealed cavity in the patient's mouth, preferably by a hollow elongate member 46 that extends between the deformable member 42 and the sealed cavity, as shown. The hollow elongate member 46 is similar to hollow elongate member 14 described above with respect to FIGS. 1A-1B. When the patient inhales, the deformable member 42 deforms and air is released into the surrounding environment from the second one-way valve. As the patient exhales, the deformable member 42 preferably simultaneously returns to the original, non-deformed state, receiving air from the patient through the hollow elongate member 46 and the first one-way valve. When a blockage occurs due, for example, to the soft tissues of the upper airway falling against the posterior pharyngeal wall, however, air removed from the sealed cavity within the patient's mouth will create a negative pressure, thereby allowing the tongue and/or other soft tissues of the upper airway to be pulled away posterior pharyngeal wall, thus removing the obstruction.

A person skilled in the art will appreciate that the negative pressure generator can have a variety of other configurations, and that a variety of other techniques can be used to create a negative pressure within a sealed cavity in a patient's mouth in response to a blocked airway.

Figure 6A:
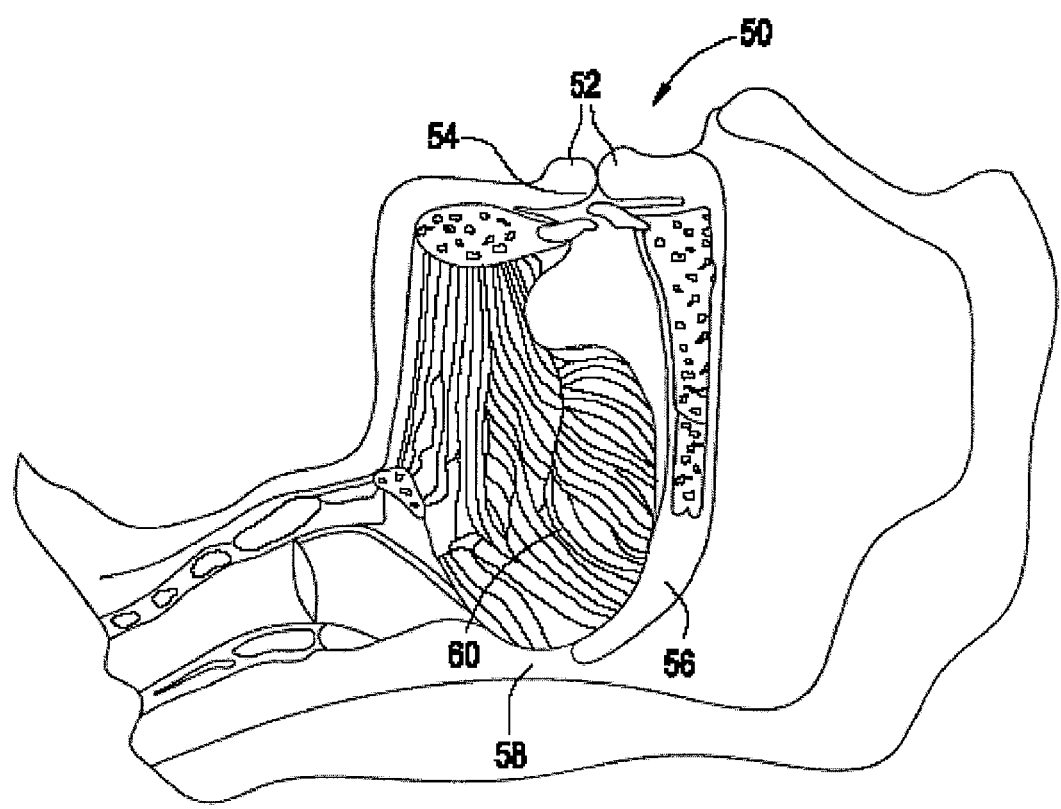
FIG. 6A is a side view illustration of the oral anatomy of a human, showing an obstructed human airway in accordance with the present invention.
Figure 6B:
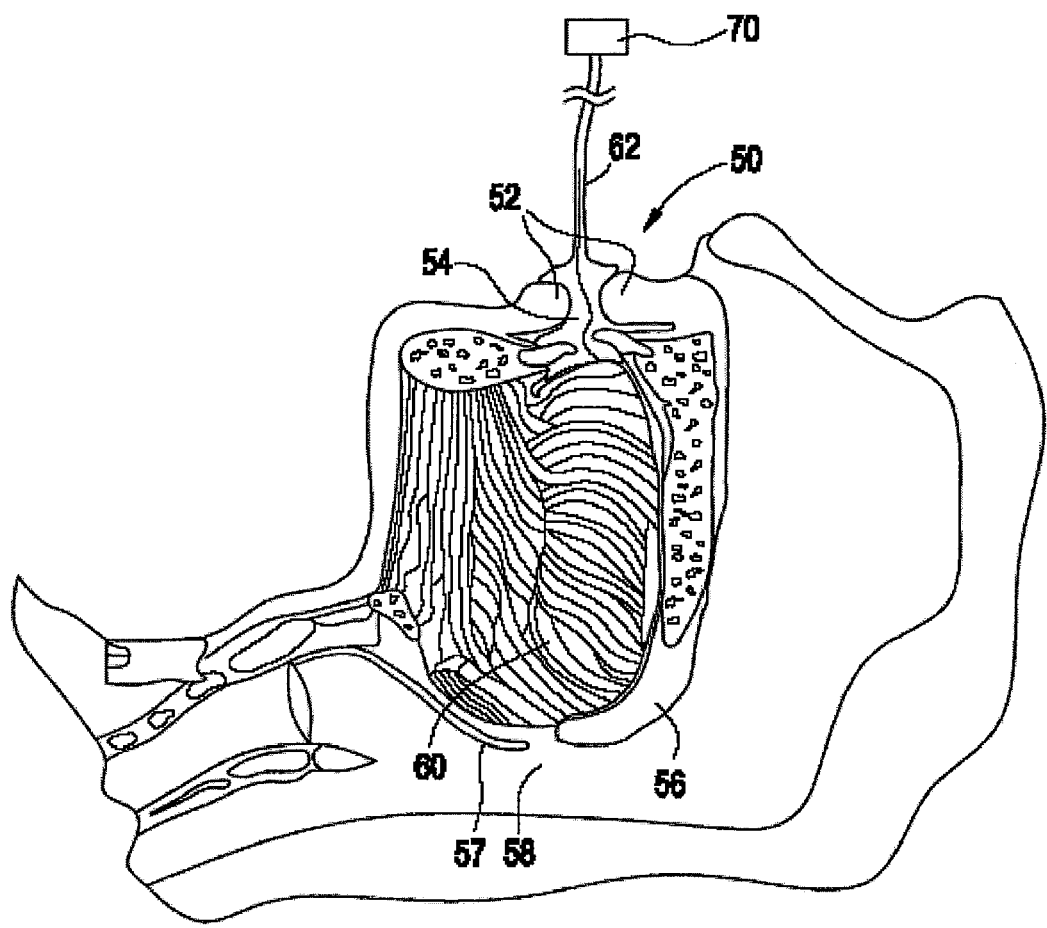
FIG. 6B is a side view illustration of the oral anatomy shown in FIG. 6A, showing the human airway after the obstruction is removed using a negative pressure generator in accordance with the present invention.

The present invention also provides methods for removing an obstruction in a human airway related to snoring and/or OSA. By way of non-limiting example, FIGS. 6A and 6B illustrate an obstructed airway, and the airway after the obstruction has been removed by a negative pressure generator, respectively. As shown, a sealed cavity 54 is formed within a patient's mouth 50, e.g., using a mouthpiece (not shown) or other suitable device, and the sealed cavity 54 is coupled to a negative pressure generator 70. The negative pressure generator 70 is then activated to withdraw air from the sealed cavity 54, preferably at a continuous rate. In an exemplary embodiment, the negative pressure generator 70 operates at a pressure in the range of about 0 to −100 cm of water, and/or it removes air at a rate of about 1 cc/minute to 50 cc/minute so that the patient does not feel any pressure when the device 70 is operating with an open airway. A person skilled in the art will appreciate that the pressure range of the negative pressure generator may vary over other ranges. For example, it may operate in a pressure range of about −1 to −50 cm of water, and more preferably at a range of about −10 to −40 cm of water. Once the patient is asleep and an obstruction of the airway occurs due, for example, to falling of the patient's tongue 60 and/or soft palate 56 against the posterior pharyngeal wall 58, as shown in FIG. 6A, the blocked airway and the mouthpiece will close the sealed cavity 54 within the patient's mouth. As a result, the negative pressure generator can remove air from the sealed cavity 54 to create a negative pressure that is effective to pull the patient's tongue 60 and/or soft palate 56 up and away from the posterior pharyngeal wall 58, thereby re-opening the airway, as shown in FIG. 6B. The negative pressure generator can also optionally be operated at a pressure that is effective to prevent the soft tissues from falling against the posterior pharyngeal wall, thus preventing an obstruction from occurring in the first place.

Figure 7:
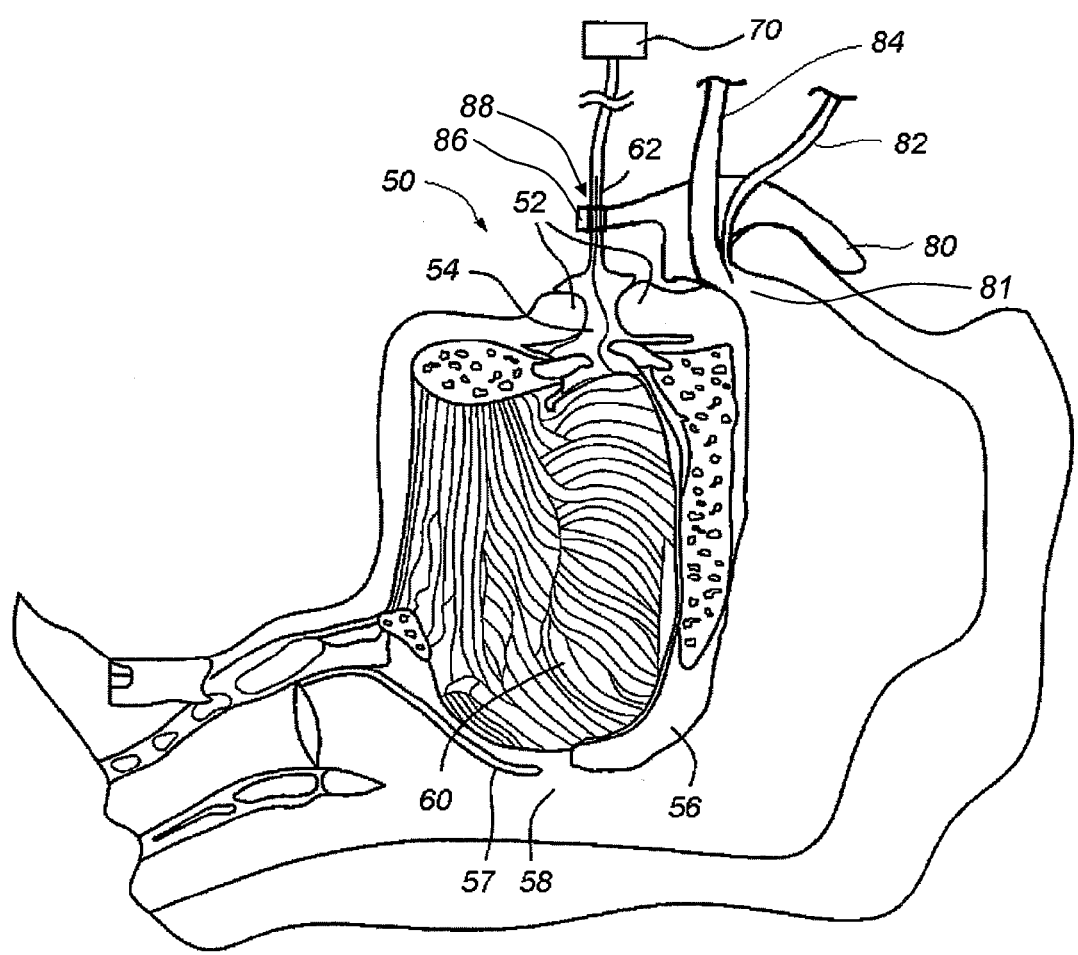
FIG. 7 is a side view illustration of the oral anatomy of a human, showing a negative pressure generator in communication with the oral airway and a nasal face mask in communication with the nasal airway in accordance with another embodiment of the present invention.

In yet another embodiment of the present invention, a mouthpiece in accordance with the present invention can be used in connection with a nasal mask or other device for ventilating the patient, or otherwise delivering gases and/or air to a patient's airway via the nasal passage. By way of non-limiting example, FIG. 7 illustrates a sealed cavity 54 formed within a patient's mouth 50, as shown in FIGS. 6A and 6B, and a nasal mask 80. While not shown, the sealed cavity can be formed using a variety of different negative pressure devices including, for example, mouthpiece 12 shown in FIGS. 1A-1B, mouthpiece 12' shown in FIG. 2, mouthpiece 112 shown in FIG. 3, or hollow body 216 shown in FIG. 4. The nasal mask 80, which is placed over the patient's nose in communication with the patient's nasal passages 81, preferably includes a first tube 84 that is adapted to connect to a device for delivering the gases and/or air, and a second tube 82 that can be used to sample $CO_2$. The mask 80 can be used in combination with a variety of devices, including, for example, CPAP devices, PEEP devices, and mechanical ventilation devices. Where the mask 80 is used to deliver gases for placing the patient under sedation or general anesthesia, the mask 80 should form a seal around the patient's nose to prevent the gases from escaping.

The nasal mask 80 can also optionally be coupled to the mouthpiece to help maintain the mask 80 and/or mouthpiece in a fixed position. As shown in FIG. 7, the nasal mask 80 includes an extension member 86 formed thereon, which has a lumen or passageway 88 extending therethrough for receiving the hollow elongate tube 62. A person skilled in the art will appreciate that a variety of other techniques can be used to couple the nasal mask 80 to the mouthpiece, and that the nasal mask 80 and the mouthpiece can optionally be integrally formed with one another. Moreover, virtually any nasal mask or other device for delivering gases and/or air to a patient's airway via the nasal passage can be used in combination with a negative pressure generating apparatus in accordance with the present invention.

In use, the mouthpiece operates as described above with respect to FIGS. 6A and 6B, and the nasal mask operates independently to deliver gases and/or air to the patient's airway via the nasal passages, and/or to allow samples to be taken for intraoperative readout. The negative pressure generated by the negative pressure generator coupled to the mouthpiece is effective to maintain an open airway by preventing the soft tissues from falling back against the posterior pharyngeal wall, thus allowing the patient to be placed under anesthesia without the risk of a blockage occurring in the patient's airway. The negative pressure generator coupled to the mouthpiece can also be effective to remove secretions from the patient's mouth. The combination of the negative pressure generator and the nasal mask can also be effective to lower gastric reflux in the patient.

One skilled in the art will appreciate further features and advantages of the invention based on the above-described elements. Accordingly, the invention is not to be limited by what has been particularly shown and described, except as indicated by the appended claims. All publications and references cited herein are expressly incorporated herein by reference in their entirety.

What is claimed is:

1. A mouthpiece for removing upper airway obstructions, comprising:
    a hollow body configured to be disposed in a user's mouth and having
        a channel formed in at least one of a superior and inferior outer surface thereof, the channel being configured to receive a user's teeth,
        an inner cavity formed therein between the superior and inferior outer surfaces and anterior and posterior surfaces and extending longitudinally between opposed ends of the hollow body, and
        at least one aperture formed in the posterior surface and extending into the inner cavity, the aperture having a width less than a width of the inner cavity such that aperture is configured to prevent a user's tongue from being pulled into the inner cavity; and
    an outer portion coupled to the hollow body and having an opening extending therethrough and in fluid communication with the cavity in the hollow body; and
    an elongate member coupled to the opening in the outer portion and having a terminal end configured to couple to a negative pressure generator.

2. The mouthpiece of claim 1, wherein the hollow body is substantially c-shaped.

3. The mouthpiece of claim 2, wherein the at least one aperture comprises a plurality of apertures spaced a distance apart from one another along the posterior surface between first and second terminal ends of the c-shaped inner portion.

4. The mouthpiece of claim 1, wherein the outer portion is configured to form a seal around a user's oral cavity.

5. The mouthpiece of claim 4, wherein the outer portion includes a flange configured to extend around a user's lips to seal the oral cavity.

6. The mouthpiece of claim 5, wherein the flange on the outer portion is spaced a distance apart from the hollow body for receiving a user's lips therebetween.

7. The mouthpiece of claim 1, wherein the at least one aperture is oriented to extend away from a user's teeth and toward a user's tongue when the mouthpiece is in use.

8. The mouthpiece of claim 1, wherein the at least one aperture includes a mesh disposed thereacross.

9. The mouthpiece of claim 1, wherein the channel includes a plurality of teeth-receiving apertures.

10. The mouthpiece of claim 1, wherein the hollow body includes a channel formed in each of the superior and inferior surfaces, and wherein a plurality of teeth-receiving apertures are formed in each channel for receiving upper and lower teeth of a user.

11. The mouthpiece of claim 1, wherein the anterior surface of the hollow body is configured to seal a user's oral cavity.

12. The mouthpiece of claim 1, wherein the opening includes a one-way valve disposed therein and configured to allow air to flow out of a user's oral cavity when in use.

13. The mouthpiece of claim 1, wherein the hollow body includes a channel formed in each of the superior and inferior surfaces, and wherein the channel in the inferior surface is positioned anterior to the channel in the superior surface.

14. A mouthpiece adapted to remove an obstruction in a human airway, comprising:
    first and second ridges defining a superior channel therebetween for receiving a user's upper teeth and an inferior channel therebetween for receiving a user's lower teeth, the first and second ridges each including an inner surface adjacent the superior and inferior channels and configured to contact a user's teeth and an outer surface configured to be oriented away from the user's teeth;
    a hollow cavity formed between the superior and inferior channels and extending longitudinally between opposed ends of the superior and inferior channels;
    at least one aperture formed in the outer surface of the second ridge and extending into the hollow cavity, the aperture having a width less than a width of the inner cavity such that the aperture has a size configured to prevent a user's tongue from being pulled into the aperture;
    an outer portion coupled to the first ridge and having an opening extending therethrough;
    an opening formed in the outer surface of the first ridge and extending into the hollow cavity, the opening being in communication with the opening in the outer portion; and
    an elongate member coupled to the opening in the outer portion and having a terminal end configured to couple to a negative pressure generator such that a negative pressure can be applied through the opening of the outer portion, through the opening formed in the outer surface of the surface ridge, and to the at least one aperture to generate a negative pressure in a user's oral cavity for relieving an obstruction in the user's airway.

15. The mouthpiece of claim 14, wherein the superior and inferior channels each include a plurality of teeth-receiving cavities formed therein.

16. The mouthpiece of claim 14, wherein the at least one aperture comprises a plurality of apertures spaced along the outer surface of the second ridge.

17. The mouthpiece of claim 14, the at least one aperture includes a mesh extending thereacross.

18. The mouthpiece of claim 14, further comprising a flange coupled to and positioned a distance apart from the outer surface of the first ridge, the flange being configured to extend around a user's lips to seal a user's oral cavity.

19. The mouthpiece of claim 14, wherein the inferior channel is positioned anterior to the superior channel.

* * * * *